United States Patent
Izumi

(10) Patent No.: US 7,292,884 B2
(45) Date of Patent: Nov. 6, 2007

(54) IMPEDANCE BASED REACTION PERFORMANCE MEASURING DEVICE

(75) Inventor: Shuichi Izumi, Asaka (JP)

(73) Assignee: Tanita Corporation, Tokyo (JP)

( * ) Notice: Subject to any disclaimer, the term of this patent is extended or adjusted under 35 U.S.C. 154(b) by 152 days.

(21) Appl. No.: 11/047,726

(22) Filed: Feb. 2, 2005

(65) Prior Publication Data

US 2005/0171450 A1  Aug. 4, 2005

(30) Foreign Application Priority Data

Feb. 2, 2004  (JP) ............................. 2004-025035

(51) Int. Cl.
A61B 5/05  (2006.01)
(52) U.S. Cl. .................................... 600/547
(58) Field of Classification Search ................ 600/547, 600/558
See application file for complete search history.

(56) References Cited

U.S. PATENT DOCUMENTS

| | | | | |
|---|---|---|---|---|
| 6,132,387 | A * | 10/2000 | Gozani et al. | 600/554 |
| 6,324,432 | B1 * | 11/2001 | Rigaux et al. | 607/62 |
| 2004/0082877 | A1 * | 4/2004 | Kouou et al. | 600/546 |
| 2004/0122702 | A1 * | 6/2004 | Sabol et al. | 705/2 |
| 2004/0133121 | A1 * | 7/2004 | Ohkura | 600/547 |
| 2004/0259494 | A1 * | 12/2004 | Mazar | 455/1 |
| 2005/0159681 | A1 * | 7/2005 | Izumi | 600/587 |
| 2006/0100540 | A1 * | 5/2006 | Gozani et al. | 600/554 |
| 2006/0184060 | A1 * | 8/2006 | Belalcazar et al. | 600/547 |

FOREIGN PATENT DOCUMENTS

| | | |
|---|---|---|
| JP | 08-184474 | 7/1996 |
| JP | 8-224226 | 9/1996 |
| JP | 2002-219117 * | 8/2002 |
| JP | 2002-219117 A | 8/2002 |

OTHER PUBLICATIONS

Botwinick, Jack., et al. "Premotor and Motor Components of Reaction Time." Database Medline Online, US National Library of Medicine (NLM), XP008046392, Database Accession No. NLM5902149, Journal of Experimental Psychology, Jan. 1966, vol. 71, No. 1, pp. 9-15.

Baylor, Ann, M., et al. "Effects of ethanol on human fractionated response times." Database Medline Online, US National Library of Medicine (NLM), XP008046331, Database AccessionNumber. NLM2920664, Drug and Alcohol Dependence, Jan. 1989, vol. 23, No. 1.

* cited by examiner

*Primary Examiner*—Max F. Hindenburg
*Assistant Examiner*—Brian Szmal
(74) *Attorney, Agent, or Firm*—McDermott Will & Emery LLP

(57) ABSTRACT

There are provided a device which can measure a reaction performance of a neurotransmission system and that of a muscle expansion/contraction system in a specific body part easily, and gives a direction that a muscle in a specific body part is to be in an unreacted state by muscle unreacted state directing means, gives a direction that the muscle in the part is to be shifted into a reacted state by muscle reacted state directing means, continuously measures impedance and time until the reaction of the muscle in the part is completed after it has been directed that the muscle in the part is to be in the reacted state by impedance measuring means and timing means, and computes the reaction time of a neurotransmission system and the reaction time of a muscle expansion/contraction system based on these continuously measured impedance and time by individual system reaction time computing means.

4 Claims, 4 Drawing Sheets

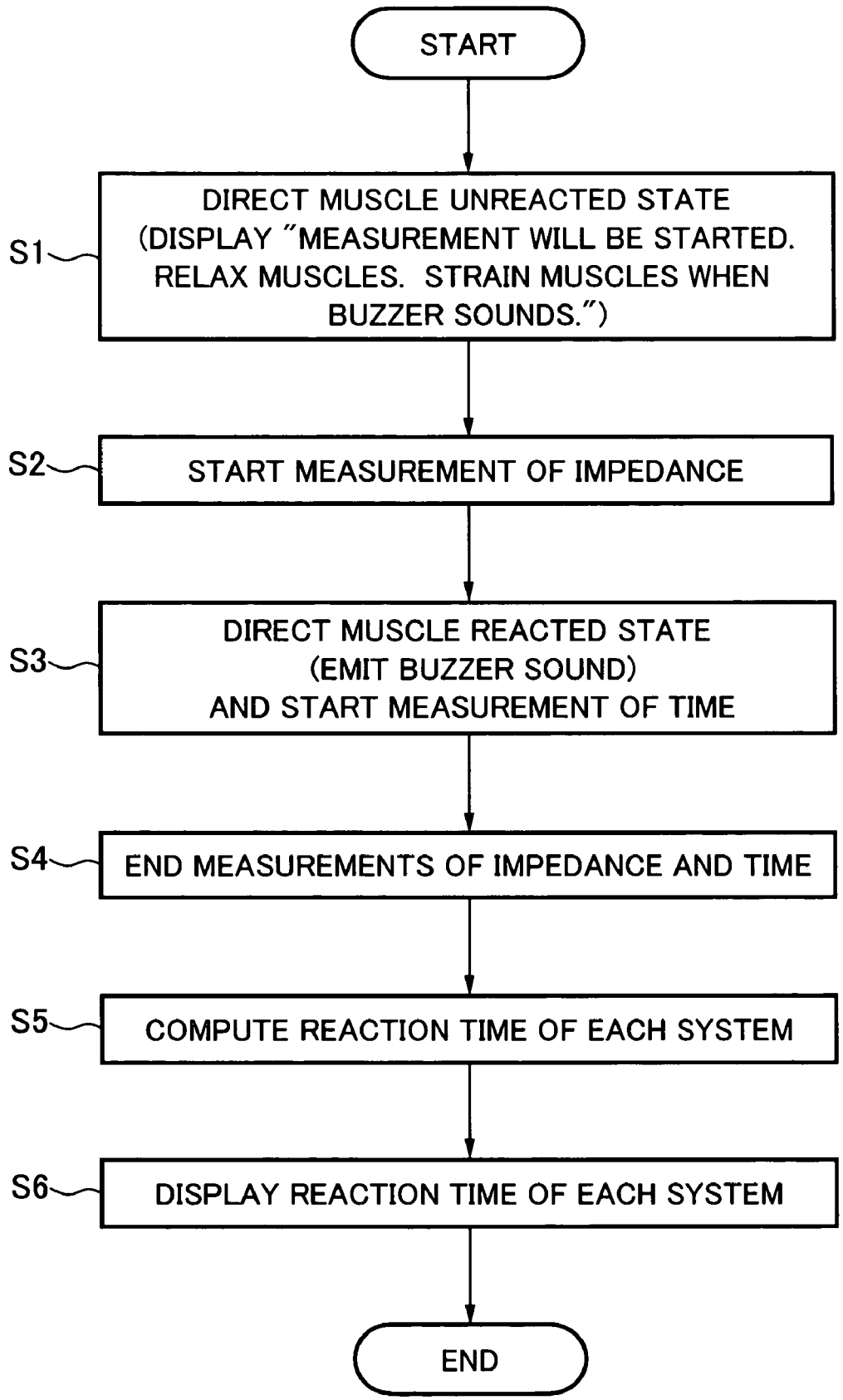

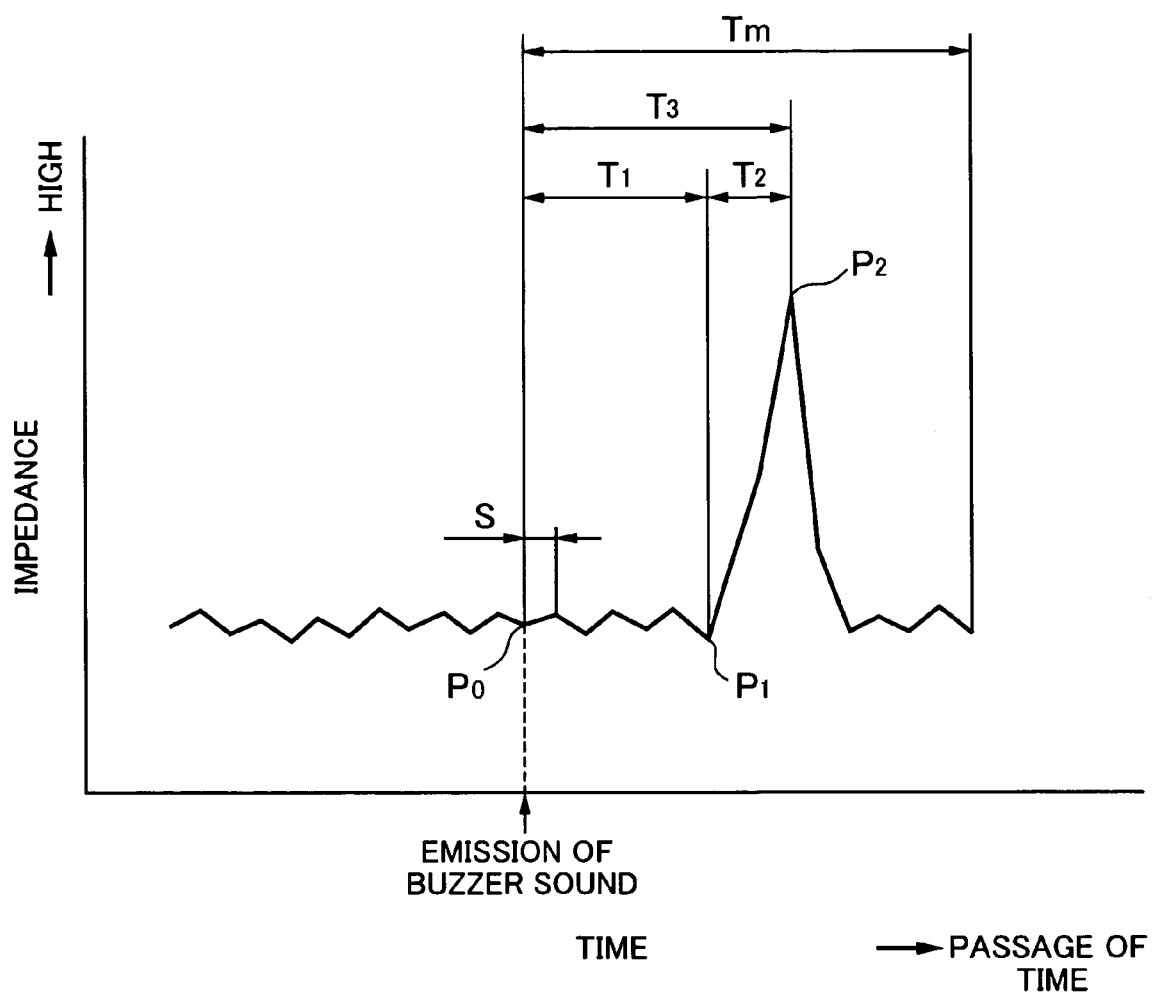

US 7,292,884 B2

IMPEDANCE BASED REACTION PERFORMANCE MEASURING DEVICE

BACKGROUND OF THE INVENTION (i) Field of the Invention

This invention relates to a measuring device which determines a reaction performance by measuring impedance.

(ii) Description of the Related Art

Conventional reaction performance measuring devices include a device as disclosed in Patent Publication 1 which determines a reaction performance by measuring a reaction time between when an indication of stimulation is seen and when the reaction of movement is detected and a device as disclosed in Patent Publication 2 which determines a reaction performance by comparing data at the time of measurement with data at normal times when buttons are pressed in accordance with data about the order of pressing.

Patent Publication 1

Japanese Patent Laid-Open Publication No. 184474/1996

Patent Publication 2

Japanese Patent Laid-Open Publication No. 224226/1996

However, the above reaction performance measuring devices merely evaluate a reaction performance including all systems associated with body reactions. That is, the devices are not capable of evaluating the reaction performance of an individual system, e.g., the reaction performance of a neurotransmission system which represents a process from when detection of signal data for a reaction is started, a signal reaches the brain and until a signal for causing a movement reaches a specific body part from the brain or the reaction performance of a muscle expansion/contraction system which represents a process from when this specific body part has received the signal from the brain and until the movement is completed.

Further, they are measuring devices which can determine only reaction performances associated with limited specific body parts, e.g., only the lower body or only hands.

Thus, in view of the above problems, an object of the present invention is to provide an impedance based reaction performance measuring device which can measure the reaction time of a neurotransmission system and the reaction time of a muscle expansion/contraction system as the reaction of a specific body part easily. Another object of the present invention is to provide an impedance based reaction performance measuring device which can also measure the reactions of specific body parts.

SUMMARY OF THE INVENTION

An impedance based reaction performance measuring device of the present invention comprises:

muscle unreacted state directing means,
muscle reacted state directing means,
impedance measuring means,
timing means, and
individual system reaction time computing means,
wherein
the muscle unreacted state directing means gives a direction that a muscle in a specific body part is to be in an unreacted state,
the muscle reacted state directing means gives a direction that the muscle in the specific body part is to be shifted into a reacted state,
the impedance measuring means has an electrode set to make contact with the specific body part and supplies a current to the specific body part and detects a voltage by use of the electrode set to continuously measure impedance until the reaction of the muscle in the specific body part is completed after the muscle unreacted state directing means has given the direction and after the muscle reacted state directing means has given the direction, the timing means continuously measures time after the muscle reacted state directing means has given the direction, and the individual system reaction time computing means computes the reaction time of a neurotransmission system and the reaction time of a muscle expansion/contraction system based on the impedance measured continuously by the impedance measuring means and the time measured continuously by the timing means.

Further, the individual system reaction time computing means computes time between a point when the muscle reacted state directing means has given the direction and a point when an increasing trend has been started in impedance changes as the reaction time of the neurotransmission system and time between a point when the increasing trend has been started in impedance changes and a point when the farthest impedance has been reached as the reaction time of the muscle expansion/contraction system, in the impedances measured continuously by the impedance measuring means after the muscle reacted state directing means has given the direction.

Further, the electrode set of the impedance measuring means is movably attached to each of specific body parts.

In the impedance based reaction performance measuring device of the present invention, the muscle unreacted state directing means and the muscle reacted state directing means give a subject a clear direction that a muscle in a specific body part is to be in an unreacted state and a reacted state, the impedance measuring means continuously measures impedance until the reaction of the muscle in the specific body part is completed after the muscle unreacted state directing means has given the direction and after the muscle reacted state directing means has given the direction by use of the electrode set which is in contact with the specific body part, the timing means continuously measures time after the muscle reacted state directing means has given the direction, and the individual system reaction time computing means computes the reaction time of a neurotransmission system and the reaction time of a muscle expansion/contraction system based on these continuously measured impedance and time. Thereby, the present device can measure the reaction time of the neurotransmission system and the reaction time of the muscle expansion/contraction system as the reaction of the specific body part easily and can be used to evaluate the reaction performance of an individual system.

Further, the individual system reaction time computing means computes time between a point when it has been directed that the muscle in the specific body part is to be in a reacted state and a point when an increasing trend has been started in impedance changes as the reaction time of the neurotransmission system and time between a point when the increasing trend has been started in impedance changes and a point when the farthest impedance has been reached as the reaction time of the muscle expansion/contraction system. Thereby, the present device can be widely used to evaluate the reaction performance of the muscle expansion/contraction system, in particular.

Further, the electrode set of the impedance measuring means can be movably attached to each of specific body parts. Thereby, the present device can determine the reaction performance of each of specific body parts.

BRIEF DESCRIPTION OF THE DRAWINGS

FIG. 3 is a flowchart illustrating the application mode and operational procedures of the device of FIG. 1.

FIG. 4 is a diagram illustrating a graph of the relationship between impedance and time before and after a direction of a muscle reacted state is given.

DETAILED DESCRIPTION OF THE PREFERRED EMBODIMENTS

An impedance based reaction performance measuring device of the present invention comprises muscle unreacted state directing means, muscle reacted state directing means, impedance measuring means, timing means and individual system reaction time computing means.

The muscle unreacted state directing means gives a direction that a muscle in a specific body part is to be in an unreacted state. The muscle reacted state directing means gives a direction that the muscle in the specific body part is to be shifted into a reacted state. The impedance measuring means has an electrode set to make movable contact with each of specific body parts and supplies a current to the specific body part and detects a voltage by use of the electrode set to continuously measure impedance until the reaction of the muscle in the specific body part is completed after the muscle unreacted state directing means has given the direction and after the muscle reacted state directing means has given the direction. The timing means continuously measures time after the muscle reacted state directing means has given the direction. The individual system reaction time computing means computes time between a point when the muscle reacted state directing means has given the direction and a point when an increasing trend has been started in impedance changes as the reaction time of a neurotransmission system and time between a point when the increasing trend has been started in impedance changes and a point when the farthest impedance has been reached as the reaction time of a muscle expansion/contraction system, in the impedances measured continuously by the impedance measuring means after the muscle reacted state directing means has given the direction.

The "unreacted state" refers to a normal muscle tension state in a given position. The "reacted state" refers to an expanded or contracted state different from normal muscle tension when a movement is made from the given position. Further, the farthest impedance refers to the maximum impedance or the minimum impedance.

Hereinafter, the impedance based reaction performance measuring device of the present invention will be further described with reference to an example.

EXAMPLES

First, a specific constitution of the impedance based reaction performance measuring device of the present invention will be described by use of an external view shown in FIG. 1 and a block diagram shown in FIG. 2.

Figure 1:
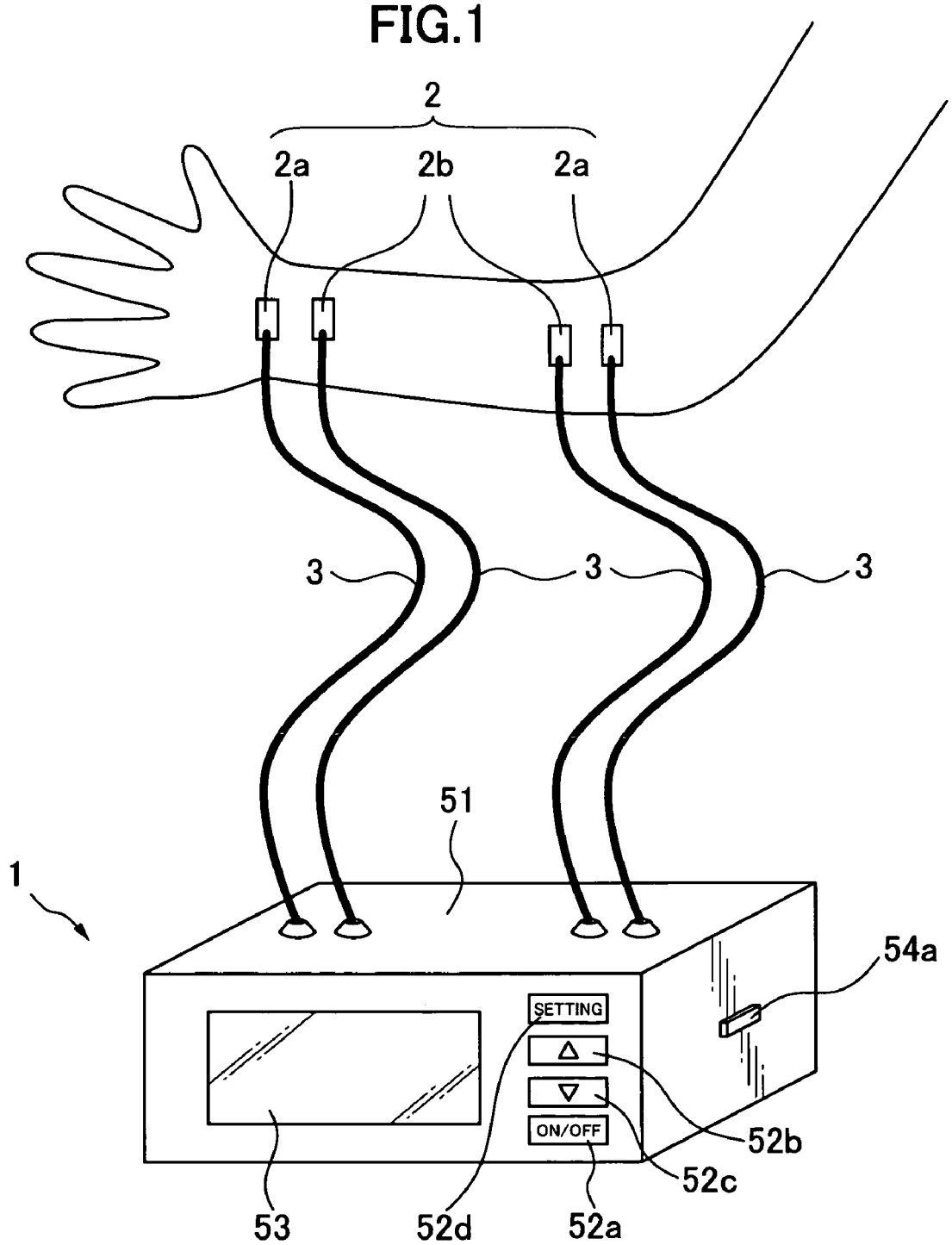
FIG. 1 is an external view of an impedance based reaction performance measuring device as an example of the present invention.

The impedance based reaction performance measuring device of the present invention roughly comprises a main unit 1, an electrode set 2, and cords 3 which connect the electrode set 2 to the main unit 1, as shown in FIG. 1.

The electrode set 2 comprises current passing electrodes 2a for passing a current through a specific body part and measuring electrodes 2b for detecting a voltage occurring during energization of a specific body part. The electrodes can be detachably attached to a specific body part.

Further, the number of the cords 3 corresponds to the number of electrodes in the electrode set 2. One end of the cord 3 is connected to the electrode 2a or 2b, and the other end thereof is connected to a circuit line of an electronic circuit card unit.

Further, the main unit 1 incorporates the electronic circuit card unit in a case 51 and has various key switches 52 (ON/OFF key 52a, UP key 52b, DOWN key 52c, setting key 52d), a display 53, and a connector 54a which constitutes a portion of an external input/output interface 54, on the external surface of the case 51.

Figure 2:
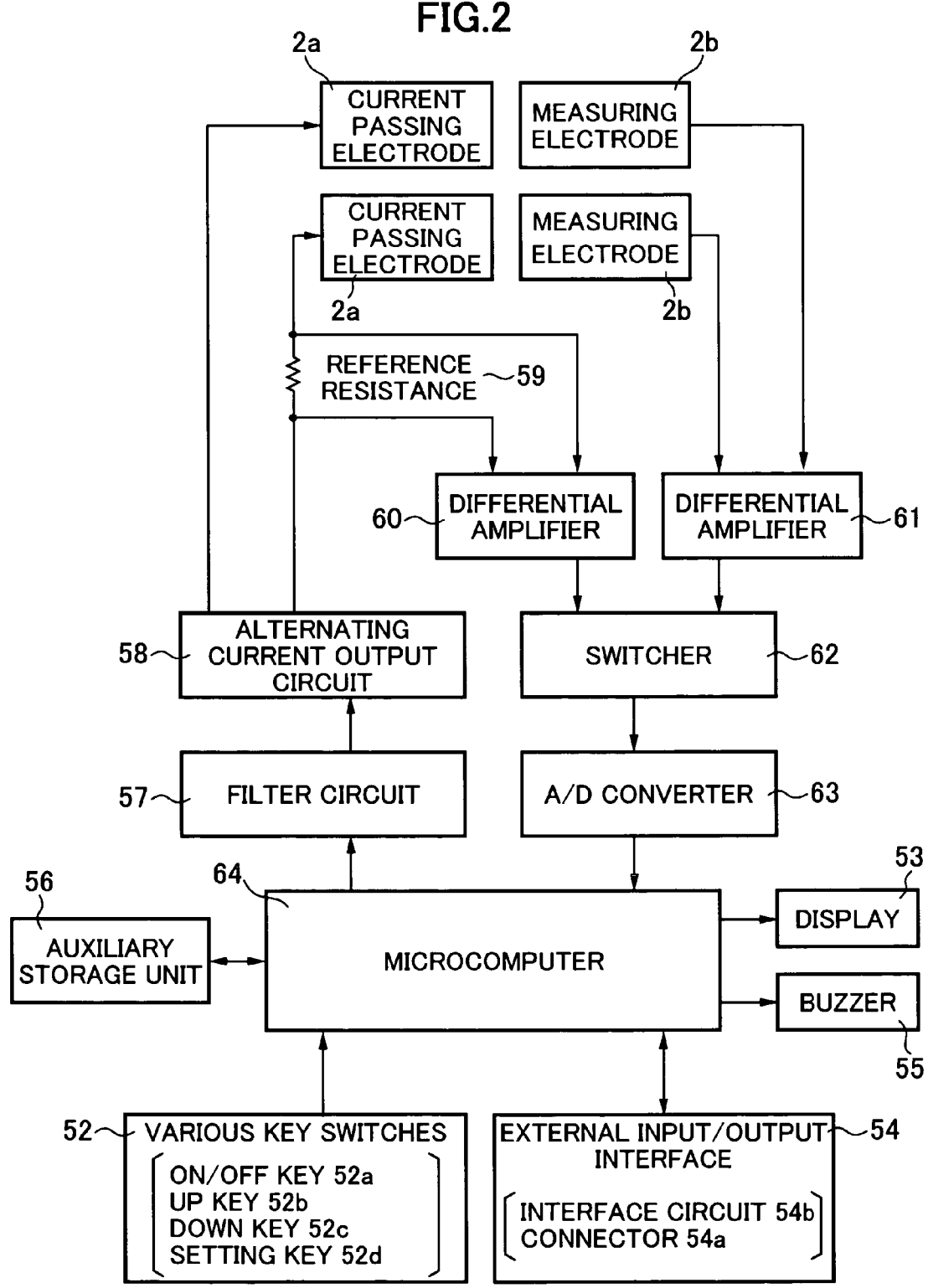
FIG. 2 is a block diagram illustrating the overall constitution of the device of FIG. 1.

The electronic circuit card unit, as shown in FIG. 2, comprises an interface circuit 54b constituting a portion of the external input/output interface 54, a buzzer 55, an auxiliary storage unit 56, a filter circuit 57, an alternating current output circuit 58, a reference resistance 59, differential amplifiers 60 and 61, a switcher 62, an A/D converter 63, and a microcomputer 64.

The display 53 displays data such as a direction of a muscle unreacted state, a direction of a muscle reacted state and the result of the reaction time of each system.

The ON/OFF key 52a is used to turn on or turn off the present device.

The UP key 52b and the DOWN key 52c are used to move a cursor at the time of input.

The setting key 52d is used to set a cursor position selected by the UP key 52b and the DOWN key 52c.

The connector 54a serves as a port to exchange data with an external device.

The interface circuit 54b exchanges signals with an external device via the connector 54a.

The buzzer 55 makes a buzzer sound as a direction of a muscle reacted state.

The auxiliary storage unit 56 stores updatable data.

The filter circuit 57 forms a signal output from the microcomputer 64 into a signal for energization.

The alternating current output circuit 58 obtains a certain execution value from a signal output from the filter circuit 57.

The reference resistance 59 is a resistance (impedance) which is connected to one output terminal of the alternating current output circuit 58 and serves as a reference for correcting the influence of change in a constant current from the alternating current output circuit 58 on impedance.

The differential amplifier 60 amplifies voltages occurring on both sides of the reference resistance 59. The differential amplifier 61 amplifies voltages detected by the measuring electrodes 2b.

The switcher 62 selects and outputs an output from the differential amplifier 60 or an output from the differential amplifier 61 under the control of the microcomputer 64.

The A/D converter 63 converts an analog signal which is an output from the switcher 62 to a digital signal and outputs the digital signal to the microcomputer.

The microcomputer 64 comprises a CPU, a ROM which stores programs for control and computation and direction data of a muscle unreacted state and a muscle reacted state, a RAM which temporarily stores computation results, programs read from external sources and input data, a timer and an I/O port. The microcomputer 64 executes processes such as measurement of the impedance of a specific body part in a muscle unreacted state or muscle reacted state, measurement of time after a muscle reacted state is directed, a direction of a muscle unreacted state or muscle reacted state, computations of the reaction time of a neurotransmission system and the reaction time of a muscle expansion/contraction system, and control relating to display of the result of the reaction time of each system. As the direction of the muscle unreacted state, a message "Measurement will be started. Relax muscles. Strain the muscles when the buzzer sounds." is displayed. The direction of the muscle reacted state is a buzzer sound.

The display 53 and the microcomputer 64 constitute muscle unreacted state directing means. The buzzer 55 and the microcomputer 64 constitute muscle reacted state directing means. The electrode set 2, cords 3, filter circuit 57, alternating current output circuit 58, reference resistance 59, differential amplifiers 60 and 61, switcher 62, A/D converter 63 and microcomputer 64 constitute impedance measuring means. The microcomputer 64 constitutes timing means and individual system reaction time computing means.

Next, an application mode and functions and operations of an impedance based reaction performance measuring device having the above constitution will be described by use of a flowchart shown in FIG. 3 and a graph shown in FIG. 4 which represents the relationship between impedance and time before and after a direction of a muscle reacted state is given.

First, when the ON/OFF key 52*a* of the case 51 of the main unit 1 is pressed, the components of the present device are activated, and the microcomputer 64 displays an initial screen on the display 53. Then, when a user inputs personal data by use of the UP key 52*b*, DOWN key 52*c* and setting key 52*d*, the microcomputer 64 displays a message "Measurement will be started. Relax muscles. Strain the muscles when the buzzer sounds." as a direction of a muscle unreacted state to the subject (STEP S1).

Then, as shown in FIG. 1, the electrodes are attached to a desired specific body part (forearm) of the subject to evaluate a reaction performance (refer to FIG. 1), and the unreacted state of a muscle (muscle related to gripping) in a given position is maintained. At the press of the setting key 52*d*, the microcomputer 64 starts measurement (sampling) of impedance in the specific body part. Then, it continuously samples the impedance of the muscle in the specific body part in the unreacted state. More specifically, the device passes a current through the specific body part (unreacted forearm muscle) of the subject from the current passing electrodes 2*a* based on a signal output from the microcomputer 64, samples impedance based on a signal level based on a voltage occurring in the specific body part (unreacted forearm muscle) and detected at that time by the measuring electrodes 2*b*, and temporarily stores the continuously sampled impedance in the RAM of the microcomputer 64 (STEP S2).

Then, as a direction of leading the subject to a muscle reacted state (i.e., causing the subject to clench the fist), a buzzer sound is emitted from the buzzer 55. Further, at the same time, the microcomputer 64 starts measurement (sampling) of time after the emission of the buzzer sound by use of the timer incorporated in the microcomputer 64 (STEP S3). The measurement (sampling) of the impedance is still continued.

Then, the microcomputer 64 continuously samples impedance in synchronization with time over a sufficiently longer time (measurement time: Tm) than time estimated to be spent by the subject to enter the muscle reacted state (i.e., clench the fist) in response to the buzzer sound. That is, it continuously samples the impedance of the specific body part in the muscle reacted state. More specifically, it samples impedance based on a signal level based on a voltage occurring in the specific body part (muscle related to gripping) and detected after the emission of the buzzer sound over the measurement time Tm at a fixed time interval S and temporarily stores the sampled impedance and time in the RAM of the microcomputer 64. Then, the microcomputer 64 ends the measurement of the impedance of the specific body part (STEP S4).

Thereafter, the microcomputer 64 computes the reaction time of each system. More specifically, the microcomputer 64 computes time between a point P0 when the buzzer sound has been emitted and a point P1 when an increasing trend has been started in impedance changes as the reaction time T1 of a neurotransmission system, computes time between the point P1 when the increasing trend has been started in impedance changes and a point P2 when the farthest impedance has been reached as the reaction time T2 of a muscle expansion/contraction system, computes a total of the reaction time T1 of the neurotransmission system and the reaction time T2 of the muscle expansion/contraction system as the reaction time T3 of the whole body reaction system, and stores the reaction times in the RAM temporarily (STEP S5). The start of the increasing trend is determined when the sampled impedance shows larger fluctuations than those in the unreacted state and shows an increase several times in a row.

Then, the microcomputer 64 displays these computed reaction times, i.e., the reaction time T1 of the neurotransmission system, the reaction time T2 of the muscle expansion/contraction system and the reaction time T3 of the whole body reaction system, on the display 53 (STEP S6). The whole operation of the present device is completed through a series of steps as described above.

In the above example, the present device is applied to measurement of the reaction of the muscle of the forearm as a specific body part. However, since the electrode set can be movably attached to each of specific body parts, the present device is also applicable to measurement of the reaction of a muscle associated with other specific body part (e.g., quadriceps femoris muscle, biceps brachii muscle or rectus abdominis muscle).

What is claimed is:

1. An impedance based reaction performance measuring device comprising:
   muscle unreacted state directing means,
   muscle reacted state directing means,
   impedance measuring means,
   timing means, and
   individual system reaction time computing means,
     wherein
       the muscle unreacted state directing means gives a direction that a muscle in a specific body part is to be in an unreacted state,
       the muscle reacted state directing means gives a direction that the muscle in the specific body part is to be shifted into a reacted state,
       the impedance measuring means has an electrode set adapted to make contact with the specific body part and supplies a current to the specific body part and detects a voltage by use of the electrode set to continuously measure impedance until the reaction of the muscle in the specific body part is completed after the muscle unreacted state directing means has given the direction and after the muscle reacted state directing means has given the direction, the timing means continuously measures time after the muscle reacted state directing means has given the direction, and the individual system reaction time computing means computes the reaction time of a neurotransmission system and the reaction time of a muscle expansion/contraction system based on the impedance measured continuously by the impedance measuring means and the time measured continuously by the timing means.

2. The device of claim 1, wherein the individual system reaction time computing means computes time between a point when the muscle reacted state directing means has given the direction and a point when an increasing trend has been started in impedance changes as the reaction time of the neurotransmission system and time between a point when the increasing trend has been started in impedance changes and a point when the farthest impedance has been reached as the reaction time of the muscle expansion/contraction system, in the impedances measured continuously by the impedance measuring means after the muscle reacted state directing means has given the direction.

3. The device of claim 1, wherein the electrode set of the impedance measuring means is movably attached to each of specific body parts.

4. The device of claim 2, wherein the electrode set of the impedance measuring means is movably attached to each of specific body parts.

* * * * *